United States Patent [19]

Edmonds et al.

[11] Patent Number: 4,590,574

[45] Date of Patent: May 20, 1986

[54] METHOD FOR DETERMINING OXYGEN AND CARBON IN SILICON SEMICONDUCTOR WAFER HAVING ROUGH SURFACE

[75] Inventors: Harold D. Edmonds, Hopewell Junction; Murlidhar V. Kulkarni, Fishkill, both of N.Y.

[73] Assignee: International Business Machines Corp., Armonk, N.Y.

[21] Appl. No.: 489,930

[22] Filed: Apr. 29, 1983

[51] Int. Cl.$^4$ .................. G06F 15/20; G06G 7/58
[52] U.S. Cl. .................. 364/498; 250/338; 356/346
[58] Field of Search ........... 364/498, 499; 356/346, 356/351; 250/338, 340, 370, 371

[56] References Cited

U.S. PATENT DOCUMENTS

| | | | |
|---|---|---|---|
| 3,553,444 | 1/1971 | Tong | 364/498 |
| 4,267,572 | 5/1981 | Witte | 364/498 |
| 4,365,303 | 12/1982 | Hannah et al. | 364/498 |
| 4,449,819 | 5/1984 | Krause | 356/300 |

OTHER PUBLICATIONS

"Computerized Infrared Spectroscopy via Fourier Transform Techniques", Koenig, J. L., American Laboratory, vol. 6, No. 9, Sep. 10, 1974, pp. 9–16.
Briska et al., IBM Technical Disclosure Bulletin, vol. 23, No. 1 (Jun. 1980), "Apparatus and Method for Determining the Carbon Content in Silicon Wafers.
Kulkarni et al., IBM Technical Disclosure Bulletin, vol. 23, No. 4 (Sep. 1980), pp. 1389–1390, "Determination of Interstitial Oxygen in Silicon Using Internal Calibration with Two Phonon Peaks".
Kulkarni et al., IBM Technical Disclosure Bulletin, vol. 25, No. 6 (Nov. 1982), pp. 2811–2812, "Purged FTIR Sample Chamber".
"American National Standard, pp. 523–524, Standard Test Methods for Substitutional Atomic Carbon Content of Silicon by Infrared Absorption, Jan. 15, 1976.
American National Standard C131.37, approved Jan. 15, 1976 by American National Standards Institute, Standard Recommended Practices for Infrared Absorption Analysis of Impurities in Single Crystal Semiconductor Materials Designation: F120–75.
American National Standard, pp. 518–520, Standard Test Method for Interstitial Atomic Oxygen Content of Silicon by Infrared Absorption, Jan. 15, 1976.
American National Standard, pp. 521–522, Standard Test Method for Interstitial Atomic Oxygen Content of Germanium by Infrared Absorption, Jan. 15, 1976.

*Primary Examiner*—Errol A. Krass
*Assistant Examiner*—Heather R. Herndon
*Attorney, Agent, or Firm*—Douglas R. McKechnie

[57] ABSTRACT

An infrared Fourier transform spectrometer is used to measure the absorbance spectrum of a sample of unknown oxygen or carbon content. From the spectrum, the roughness of the wafer is defined, and such roughness definition is then used to calculate the oxygen or carbon content. The roughness can be defined by using the slope of the absorbance spectrum or by the degree of shift of the baseline of the oxygen or carbon peak.

10 Claims, 5 Drawing Figures

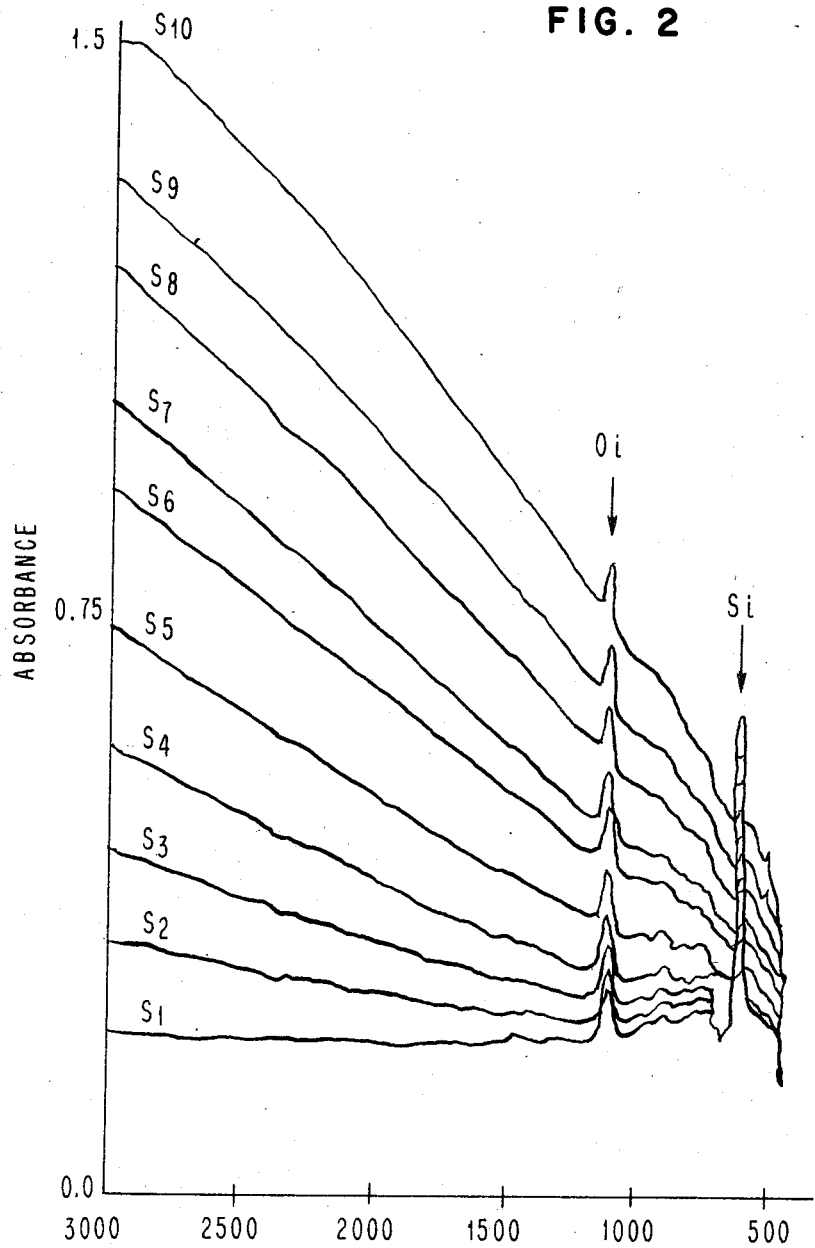

METHOD FOR DETERMINING OXYGEN AND CARBON IN SILICON SEMICONDUCTOR WAFER HAVING ROUGH SURFACE

FIELD OF THE INVENTION

This invention relates to measuring the carbon and oxygen content of semiconductor wafers by infrared (IR) absorbance techniques. More particularly it relates to improvements in methods for measuring wafers having rough or non-polished surfaces.

PRIOR ART

The measurement of the carbon and oxygen content of silicon wafers by IR absorbance at certain wavelengths, is a known technique that can be readily done by IR Fourier transform (FT) spectroscopy. When both sides of a wafer are polished, the method provides accurate results provided a correction is made for multiple reflections in the wafer. However, if one side is not polished, the degree of correction due to a lesser amount of multiple reflections, is somewhat indefinite and the resultant measurement may be as much as 15% in error.

The problem was recognized and a solution described in "Determination of Interstitial Oxygen in Silicon using Internal Calibration with Two Phonon Peaks", by G. K. Agopian and M. V. Kulkarni, IBM TDB Vol. 23, No. 4 (September 1980), pages 1389-1390. However, use of such method produces results that may still be quite high in error.

SUMMARY OF THE INVENTION

Accordingly, one of the objects of the invention is to provide a method for measuring the carbon and oxygen content of a semiconductor wafer having at least one rough or non-polished side, which method is more accurate than prior methods known to us.

Another object is to provide a method of characterizing the degree of roughness of a wafer to determine a correction factor usable in accurately measuring the carbon and/or oxygen content of the wafer.

Briefly, in accordance with the method, an IRFT spectrometer is used to measure the absorbance spectrum of a sample of unknown oxygen or carbon content. From the spectrum, the roughness of the wafer is defined, and such roughness definition is then used to calculate the oxygen or carbon content. The roughness can be defined by using the slope of the absorbance spectrum or by the degree of shift of the baseline of the oxygen or carbon peak.

Other objects and advantages of the invention will be apparent from the following description taken in connection with the accompanying drawings wherein:

FIG. 2 are curves of different absorbance spectrums, useful in understanding the invention;

Figure 1:
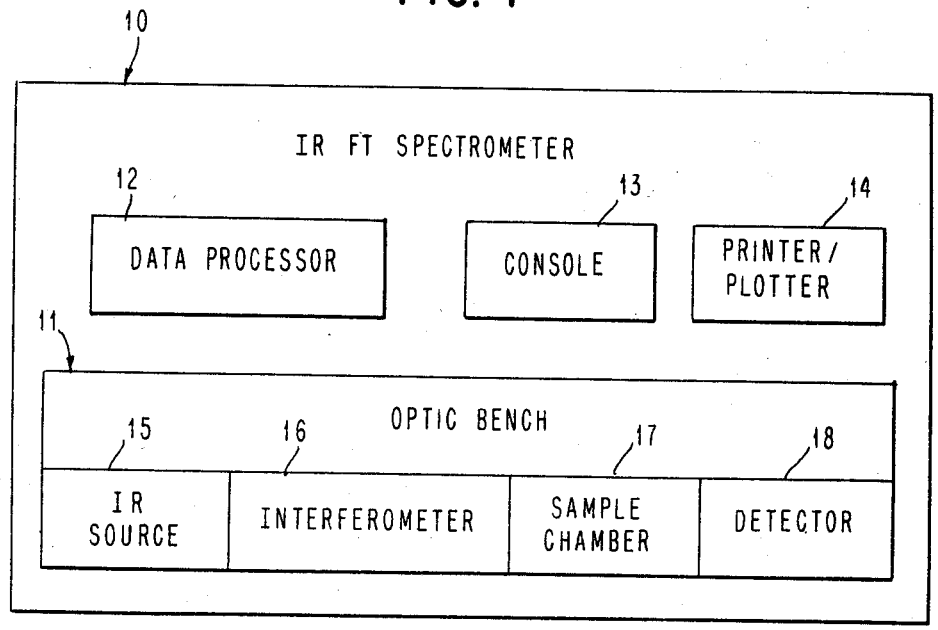
FIG. 1 is a schematic diagram of apparatus used to perform the method of the invention.

Referring now to the drawings, the method of the invention is performed using the apparatus shown in FIG. 1. The apparatus is a conventional IRFT spectrometer 10 modified as described below. Spectrometer 10 generally comprises an optic bench 11, data processor 12, an operators console 13 and a printer or plotter 14. The optic bench, in turn, comprises an IR source 15, interferometer 16, sample chamber 17 and detector 18. Spectrometer 10 may be, for example, an IR/85 Model 2A spectrometer commercially available from IBM Instruments Inc. and having a sample chamber 17 modified as described in "Purged FTIR Sample Chamber", by R. H. Cadwallader and M. V. Kulkarni, IBM TDB Vol. 25, No. 6, November 1982, pages 2811-2812, to permit the rapid insertion of a semiconductor wafer into a purged atmosphere and in the path of the IR energy, for analysis. Data processor 12 is a general purpose data processing system in which various programs are stored as signals for operating the system, and the invention involves modifying the stored programs by adding thereto appropriate programs or signals for performing the method described below.

The general operation of the system thus far described is well known. A wafer to be measured is inserted into sample chamber 17 and after sufficient time has passed insuring that the sample is in a purge gas atmosphere, interferometer 16 is actuated so as to produce a time varying signal at the output of detector 18 which is known as an interferogram. The output of the detector in analog form, is first digitized and then stored in data processor 12. By mathematical manipulation, including a Fourier transform, the interferogram is converted to a frequency domain signal representing the intensity of the IR energy at different wavelengths. An absorbance spectrum is produced by first measuring the incident IR energy without any wafer in the sample chamber and the resultant spectrum thereof is used to calculate how much IR energy was absorbed by the wafer at each of the different wavelengths. The output is the well known absorbance spectrum.

The method of the invention is useful for determining both the carbon and the oxygen content of the wafer. The method for determining the carbon is the same as that for the oxygen, except for the specific wavelengths at which the carbon peaks are measured, so the method will be described relative to that which occurs when measuring only the oxygen content.

The invention is based upon the discovery resulting from investigations of the effect of surface roughness upon measured absorbance spectrums. These investigations produced the graph shown in FIG. 2, which is a graph of absorbance spectrums of a silicon wafer having a known thickness (24.6 mils) and a known oxygen content (30.0 ppma), measured in the following manner. The first measurement (spectrum S1) was made when both sides of the wafer were in a polished condition. Such a wafer is known as a DSP (double side polished) wafer. Next, one side of the wafer was abraded for a fixed period of time, to roughen the surface. A second measurement (spectrum S2) was made. The wafer was again abraded in the same manner as before, and another measurement was made. The steps of abrading and measuring was continued until a total of ten measurements (spectrums S1-S10) were made. The results were plotted to produce the graph of FIG. 2. From the results the following observations and conclusions were made.

First, the repetitive abrasion produced a surface of increasing roughness.

Second, the general slopes of the spectrums increased with increasing roughness. Thus, the slope of a spectrum is a measure of the degree of surface roughness.

Third, with increasing roughness, the absorbance of the point on the baseline of the oxygen peak, at 1107 cm$^{-1}$, increases so that such absorbance could also be used as a measure of the degree of roughness.

Fourth, the height of the oxygen peak decreased exponentially.

Figure 4:
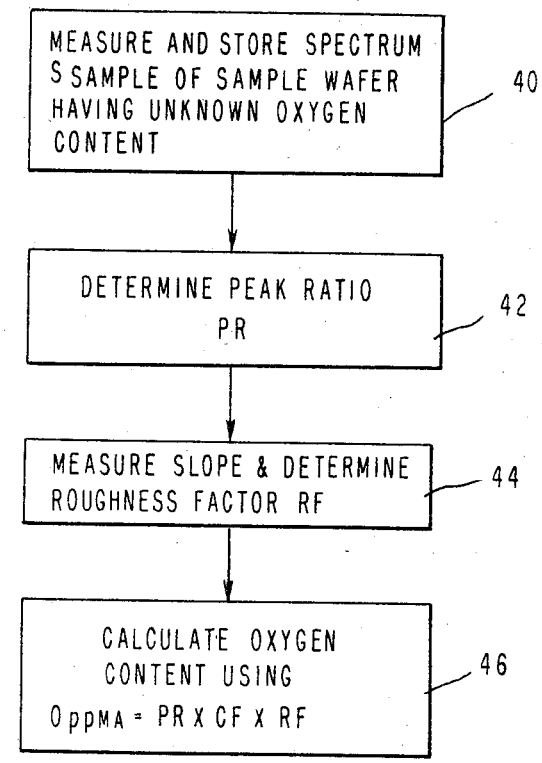
FIG. 4 is a flow chart of the measurement method of the invention.
Figure 3:
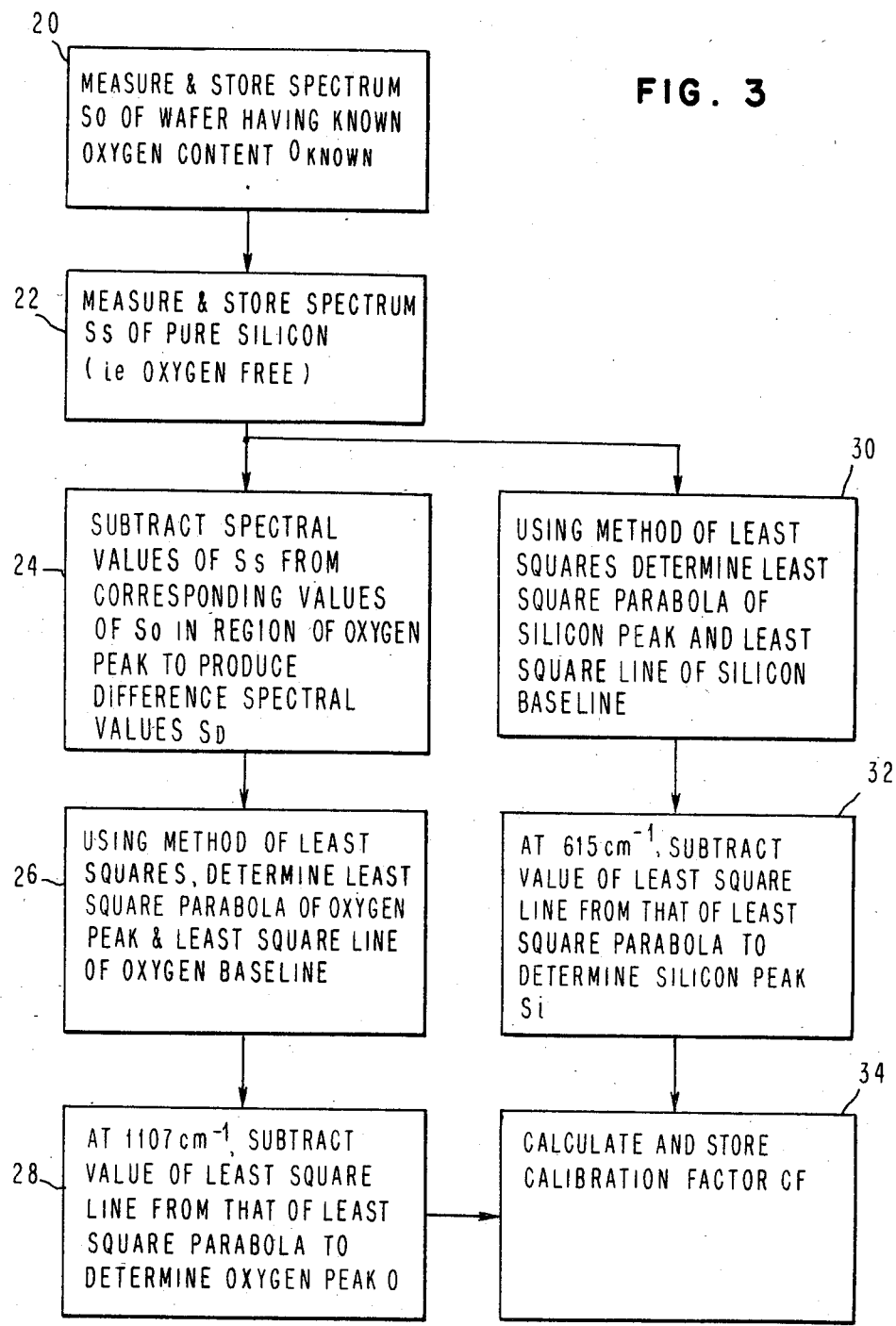
FIG. 3 is a flow chart of the calibration method of the invention.

The investigations also concluded that the oxygen content can be calculated in accordance with the following equations:

$$O_{ppma} = PR \times CF \times RF \qquad \text{Eqn. 1}$$

where
PR = peak ratio of oxygen to silicon peaks
CF = Calibration Factor
RF = roughness factor $$RF = \frac{1}{.94 - .06e^{-SLOPE}} \qquad \text{Eqn. 2}$$

where
e = base of natural log $$SLOPE = \frac{A_o - A_s}{t} \qquad \text{Eqn. 3}$$

where
$A_o$ = absorbance on baseline at 1040 cm$^{-1}$
$A_s$ = absorbance on baseline at 700 cm$^{-1}$
t = thickness of sample in centimeters The signficance of the above equations and manner of their use will be best understood from the following description of the method of the invention, made relative to FIGS. 3 and 4.

The method of the invention includes a preliminary or calibration process (shown in FIG. 3), and the actual measurement process (shown in FIG. 4) used to determine the oxygen content of a wafer having an unknown amount of oxygen. In accordance with step 20, a wafer having a thickness within + or −5 mils of the thickness of the sample wafer eventually to be measured, is placed in the spectrometer 10 and its absorbance spectrum is determined in the conventional fashion. This produces a spectrum So which is a series of digitized values of absorbance at different wavelengths, dependent upon the resolution of the spectrometer. The wafer is polished on both sides and has a known oxygen content $O_{KNOWN}$. The digitized values are stored in the memory of the processor. In step 22, a wafer of pure silicon is next placed in the spectrometer and its absorbance spectrum measured. Such wafer has both sides polised, is oxygen free and provides a spectrum of high purity silicon. These digitized values $S_s$ are also stored in the processor. Quite obviously, step 22 can be reversed in time sequence with step 20. The pure silicon wafer is also polished on both sides and both steps 20 and 22 are carried out under the same temperature conditions and resolutions.

Step 24 is carried out in the processor and the spectral values of $S_s$ are subtracted from a corresponding values of $S_o$ within the region of the oxygen peak, to produce spectral values $S_d$ that represent the difference between $S_o$ and $S_s$. This region would be sufficiently wide so that spectral values $S_d$ include not only the oxygen peak itself but also baseline values to either side thereof.

Next, using the conventional well-known method of least squares, the formula for the least square parabola of the oxygen peak center around 1107 cm$^{-1}$, is calculated. This might include taking a total of, for example, five values to either side of the center. Also, the baseline values of $S_d$ are analyzed to determine the formula for the least square line of the oxygen baseline. In step 28, using the least square formulas from step 26, the values of the least square line at 1107 cm$_{-1}$ is subtracted from that of the least square parabola at the same wavelength, to determine oxygen peak O.

Steps 24 and 30 also use the output of steps 20 and 22. For step 24, the two spectrums $S_o$ and $S_s$ may have to be scaled relative to one another to produce accurate results. The scaling can be done by using the silicon peak of either one. If the peaks have both the same values, then step 24 can be done without scaling but if the peaks have different values, then the values of one spectrum have to be scaled by multiplying by the ratios of the two silicon peaks. Step 30, in a manner similar to step 26, involves using the method of least square to determine the least square parabolic formula for the silicon peak and the least square line for the silicon baseline. Using these formulas then, step 32 subtracts the values of the least square base or line from that of the least square parabola, determined at 615 cm$_{-1}$ to thereby determine the silicon peak $S_i$. In step 34, the calibration factor CF is then calculated and stored. The calculation is done using Eqn. 4. The ratio of $O/S_i$ is the peak ratio and the calibration factor CF is simply that factor by which the peak ratio would be multiplied to arrive at the known oxygen content.

$$O_{KNOWN} = \frac{O}{S_i} \times CF \qquad \text{Eqn. 4}$$

Steps 20–34 may be thought of as the calibration process and provides two factors used later in the measurement process. These factors are the spectrum $S_s$ of pure silicon and the calibration factor CF. With these factors stored in a processor, the measurement process illustrated in FIG. 4 can then be accomplished. In step 40, the absorbance spectrum $S_{SAMPLE}$ of a sample wafer having an unknown oxygen content, is measured. The measurement takes place under the same temperature and resolution conditions as that of steps 20 and 22. The sample wafer should have a thickness within + or −5 mils of that of the wafers used in the calibration process. The sides of the wafer may be polished or non-polished, i.e., having some degree of roughness from a polished condition.

Next, the peak ratio PR is determined in step 42, by a process similar to that of steps 24–32. In accordance with these steps, the values of the measured spectrum of pure silicon, from step 22, in the oxygen region, are subtracted from the corresponding values of $S_{SAMPLE}$. The peak parabola and baseline are determined using the least square method and the oxygen peak then measured at the same wave number. The same thing is done for the silicon peak for the sample and the peak ratio is then calculated as the value of the oxygen peak divided by the value of the silicon peak.

Next, in step 44, the slope associated with spectrum $S_{SAMPLE}$ is measured or determined in accordance with Eqn. 3 from which the roughness factor RF is calculated in accordance with Eqn. 2. The roughness factor compensates for an exponential decay in values because of increasing roughness. Finally, in step 46, the oxygen content of the sample is then calculated from Eqn. 1 by multiplying the peak ratio PR times the calibration factor CF times the roughness factor RF. It is to be appreciated that the slope used in the above calculations is determined in a specific manner by measuring the absorbance on the baseline at 1040 and 700 wave numbers. It should be also appreciated that other measures of the degree of roughness can be used or other ways of measuring the slopes, which should be apparent from the foregoing discussion of FIG. 2. If other ways are used, then the calculation of the roughness factor RF in FIG. 2 would have to be adjusted to compensate for the different values used. It should be also noted that from FIG. 2, a double polished wafer has a relatively flat spectrum and hence has no slope. With a zero slope, Eqn. 2 reduces to RF=1, and hence the calculation for a double polished wafer becomes simply that of multiplying the peak ratio PR by the calibration factor CF. In other words, the method applies to both polished and unpolished wafers.

The carbon content is determined in the same manner, by using a wafer of known carbon content during the calibration process, determing and using the carbon peak instead of the oxygen peak, in the calculations.

The above described method is based on the previously enumerated observation that the slope of the absorbance spectrum defines the degree of roughness. An alternative method, the description of which follows, is based on the above fourth observation that the roughness can be defined by the degree of shift of the baseline of the oxygen peak.

In carrying out the alternative method, the following equations are used:

$$O_{TRUE} = O_{MEASURED} - MRC \times RF'$$  Eqn. 5 where $O_{TRUE}$ is the oxygen content in PPMA being measured
$O_{MEASURED}$ is defined in Eqn. 6
MRC is defined in Eqn. 8
RF' is defined in Eqn. 7

$$O_{MEASURED} = \frac{O \times 2.303 \times 9.63}{t}$$  Eqn. 6 where

O is the oxygen peak absorbance above baseline (step 28)
t is the thickness (in cm) of the wafer $$RF' = e^{-IF \times \Delta a_b}$$  Eqn. 7 where

RF' is roughness factor
IF is instrumental factor in the range $0.1 < IF < 0.13$ and $\Delta a_b$ is as defined below by Eqn. 10.

$$MCR = \frac{9.63}{t} \ln \frac{1 - R^2 e^{-2(a_p + a_b 1)t}}{1 - R^2 e^{-2 a_b 1 \, t}}$$  Eqn. 8 where

MRC = multiple reflection contribution
$a_b{}^1$ = absorption coefficient measured on DSP oxygen free wafer at 1107 cm$^{-1}$, using Eqn. 11

$a_b{}^2$ = absorption coefficient measured on sample at 1107 cm$^{-1}$ on the baseline of oxygen peak using Eqn. 11
$a_p$ = impurity absorption coefficient by Eqn. 9

$$a_p = \frac{O \times 2.303}{t}$$  Eqn. 9

$$\Delta a_b = a_b{}^2 - a_b{}^1$$  Eqn. 10

$$10^{-A} = T = \frac{(1 - R)^2 e^{-at}}{1 - R^2 e^{-2at}}$$  Eqn. 11 where

Figure 5:
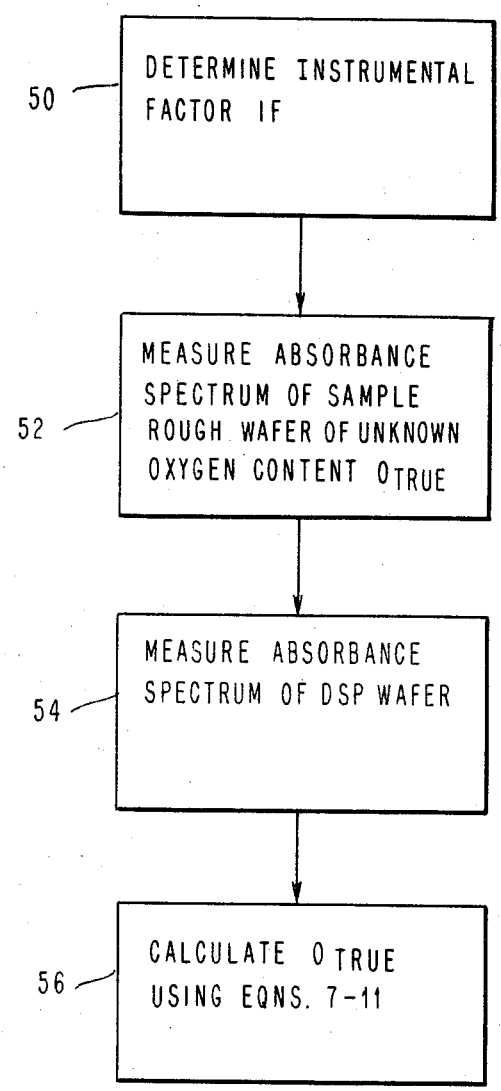
FIG. 5 is a flow chart of an alternative method of the invention.

A = absorbance
T = transmittance
R = reflectivity
$\alpha$ = absorption coefficient, cm$^{-1}$ A, t and $\alpha$ are applied with corresponding super- and sub-scripts The significance of these equations will now be described in terms of how they are used during the process. Referring to FIG. 5, the instrumental factor IF is determined by step 50. IF is empirically obtained on a given instrument by measuring a sample having a known oxygen content for varying degrees of roughness and applying the above equations to solve for IF. This factor will be substantially constant for a given instrument but varies from instrument to instrument and lies in the range $0.1 < IF < 0.13$. IF has to be determined only once for a given instrument.

Next, in step 52, a sample wafer having at least one non-polished or rough surface, an unknown oxygen content $O_{TRUE}$ and a thickness t, is placed in the spectrometer and its spectral absorbance is measured. Its absorbance $A_b{}^2$ at 1107 cm$^{-1}$ on oxygen baseline is determined and such value is placed in Eqn. 11 to solve for the absorption coefficient $a_b{}^2$. Also, the oxygen peak O is determined in the same manner as it is by the first method described above relative to steps 24–28. The next step 54 is to measure the spectral absorbance of a sample of any oxygen content including zero, but having both sides polished. The absorbance $A_b{}^1$ at the baseline point 1107 cm$^{-1}$ is determined and such value is then entered in Eqn. 11 to solve for absorption coefficient $a_b{}^1$.

Finally, in step 56, a series of calculations are performed to arrive at the desired value of $O_{TRUE}$. The series includes determining $\Delta a_b$ by Eqn. 10 using the values of $a_b{}^1$ and $a_b{}^2$ determined in step 54. The roughness factor RF' is then calculated by Eqn. 7. The oxygen peak O is used in Eqn. 9 to calculate $a_p$ and the multiple reflection contribution MRC (is calculated from Eqn. 8. Using the oxygen peak O Eqn. 6 is solved for $O_{MEASURED}$. Lastly, $O_{TRUE}$ is determined from Eqn. 5 using the values of $O_{MEASURED}$, MRC, and RF' from above.

In summary, at the start of the method, the following factors are known: t, IF, R & $\Delta a_b$. From the measured absorbance spectrums of the rough sample wafer and the DSP wafer, the absorbances $A_b{}^1$ and $A_b{}^2$, and the oxygen peak O are determined. Then, using all these values and factors in eqns. 5-11, the desired oxygen content $O_{TRUE}$ is obtained.

The above equations Eqn. 1-11 are herein considered to be definitions thereof and any mention of specific equations 1-11 in the claims, means the specific definitions set forth in the above specification. It should be obvious that other equations, which differ from the above by merely using different constants or derivative terms, are considered to be equivalent. Furthermore, the calculations using such equations are done in the data processor 12 of spectrometer 10, by suitable program using conventionally known programming techniques to solve the equations in straight forward fashion.

It should be obvious that other changes can be made in the details and arrangements of the steps of the invention without departing from the scope of the invention.

Having thus described our invention, what we claim as new and desire to secure by Letters Patent is:

1. The method for determining the element content of oxygen and carbon in a sample semiconductor wafer having at least one rough surface, by means of an IRFT spectrometer including a data processing system, comprising the steps, carried out by said spectrometer, of:
   (a) measuring an absorbance spectrum of the sample wafer and storing digitized values of said spectrum in said data process system, said spectrum comprising absorbance values at different wavelengths of infrared energy;
   (b) deriving, in said data processing system, from said digitized values of said spectrum a roughness factor proportional to the degree of roughness of said rough surface;
   (c) and determining in said data process system the content of oxygen and carbon in said sample wafer by means of said roughness factor.

2. The method of claim 1 wherein said roughness factor is derived from a slope of said values of said spectrum.

3. The method of claim 2 wherein said slope is determined by a rate of change in absorbance at a predetermined wavelength.

4. The method of claim 1 wherein said roughness factor is derived from an exponential decrease in an element peak, of said spectrum, due to the degree of roughness of said rough surface.

5. The method of claim 1 comprising:
   (d) measuring a second absorbance spectrum of a double sided polished second wafer free of the element in the sample wafer, and storing digitized values of said second absorbance spectrum in said data processing system;
   (e) subtracting said stored values of said second absorbance spectrum from the corresponding values of the sample spectrum stored in step (a) to produce values of a difference spectrum; and
   (f) determining an absorbance peak due to an element from the difference spectrum of step e.

6. The method of claim 5 wherein step (f) comprises: determining a baseline value at a wavelength associated with the peak of the element, and subtracting said baseline value from the absorbance value in said difference spectrum at such wavelength.

7. The method of claim 6 wherein said baseline value and said absorbance value at said wavelength, are determined by a method of least squares curve fitting.

8. The method of claim 5 comprising:
   (g) measuring a third absorbance spectrum of a polished wafer having a known element content, and storing digitized values thereof in said data processing system;
   (h) deriving, in said data processing system, a calibration factor from said stored values of said third spectrum, equating a ratio of an absorbance peak due to an element to an absorbance peak due to the base material of a wafer;
   and step (c) is performed using said calibration factor from step (h).

9. The method of claim 8 wherein said roughness factor in step (b) is calculated by measuring a slope of said sample spectrum.

10. The method of claim 5 comprising:
    (g) measuring a third absorbance spectrum of a double sided polished wafer, and storing digitized values of said third absorbance spectrum in said data processing system; and
    (h) deriving from third spectrum a second absorbance peak corresponding to said absorbance peak from step (f);
    said roughness factor being determined from the decrease in absorbance peak from step (f) due to the roughness of said rough surface, relates to said second absorbance peak of said polished wafer on which said third absorbance spectrum is measured.

* * * * *